(12) United States Patent
Lyon

(10) Patent No.: US 8,986,220 B2
(45) Date of Patent: Mar. 24, 2015

(54) SPINAL ASPIRATION APPARATUS

(76) Inventor: Thomas R. Lyon, Brooklyn, NY (US)

(*) Notice: Subject to any disclaimer, the term of this patent is extended or adjusted under 35 U.S.C. 154(b) by 651 days.

(21) Appl. No.: 12/676,414

(22) PCT Filed: Sep. 2, 2008

(86) PCT No.: PCT/US2008/010743
§ 371 (c)(1),
(2), (4) Date: Mar. 4, 2010

(87) PCT Pub. No.: WO2009/032353
PCT Pub. Date: Mar. 12, 2009

(65) Prior Publication Data
US 2010/0185117 A1    Jul. 22, 2010

(30) Foreign Application Priority Data
Sep. 4, 2007 (WO) .................. PCT/US07/19267

(51) Int. Cl.
*A61B 10/00* (2006.01)
*A61B 17/34* (2006.01)
*A61B 10/02* (2006.01)

(52) U.S. Cl.
CPC ..... *A61B 17/3403* (2013.01); *A61B 2010/0258* (2013.01); *A61B 2017/3407* (2013.01); *A61B 2017/3411* (2013.01)
USPC ........................................................ 600/562

(58) Field of Classification Search
USPC ............... 600/562–567, 570–571; 604/22
See application file for complete search history.

(56) References Cited

U.S. PATENT DOCUMENTS

| 2,531,734 A | 11/1950 | Hopkins |
| 4,709,705 A | 12/1987 | Truglio |
| 4,808,157 A | 2/1989 | Coombs |
| 5,012,818 A | 5/1991 | Joishy |
| 5,282,477 A | 2/1994 | Bauer |
| 5,357,974 A | 10/1994 | Baldridge |

(Continued)

FOREIGN PATENT DOCUMENTS

| CN | 1058142 | 1/1992 |
| EP | 0513446 | 2/1991 |

(Continued)

OTHER PUBLICATIONS

Aspiration to Obtain Osteoblast Progenitor Cells from Human Bone Marrow: The Influence of Aspiration Volume* by George F. Muschler, et al., The Journal of Bone and Joint Surgery (1997).

(Continued)

*Primary Examiner* — Rene Towa
(74) *Attorney, Agent, or Firm* — Harold G. Furlow, Esq

(57) ABSTRACT

A spinal aspiration apparatus 10 is described that includes a needle 11 that has a shape suitable for the location of and penetration through a pedicle pathway of a vertebra 1. The distal end portion of the spinal aspiration apparatus 10 includes a plurality of apertures that are in fluid communication with a lumen 24 of needle 11. The size and angular orientation of the apertures are constructed using the principles of fluid mechanics to create separate and distinct harvest volumes of bone marrow 4 within a body 2 of vertebra 1. A proximal end portion 14 of needle 11 includes an external interface 17 that is adapted to provide a fluid tight coupling with an external source of reduced pressure. A handle 16 is connected to proximal end portion 14 that aids in the manipulation of needle 11.

20 Claims, 10 Drawing Sheets

(56) References Cited

U.S. PATENT DOCUMENTS

| | | | |
|---|---|---|---|
| 5,372,583 A | 12/1994 | Roberts et al. | |
| 5,474,558 A | 12/1995 | Neubardt | |
| 5,660,186 A | 8/1997 | Bachir | |
| 5,701,910 A * | 12/1997 | Powles et al. | 600/577 |
| 5,954,671 A | 9/1999 | O'Neill | |
| 6,022,324 A | 2/2000 | Skinner | |
| 6,210,376 B1 | 4/2001 | Grayson | |
| 6,413,228 B1 | 7/2002 | Hung et al. | |
| 6,425,887 B1 | 7/2002 | McGuckin et al. | |
| 6,554,803 B1 | 4/2003 | Ashman | |
| 6,558,353 B2 | 5/2003 | Zohmann | |
| D489,456 S | 5/2004 | Groenke et al. | |
| 6,770,070 B1 | 8/2004 | Balbierz | |
| 6,887,246 B2 | 5/2005 | Bhatnagar et al. | |
| 6,890,308 B2 | 5/2005 | Islam | |
| 6,916,292 B2 | 7/2005 | Morawski et al. | |
| 7,066,942 B2 | 6/2006 | Treace | |
| 7,175,336 B2 | 2/2007 | Voellmicke et al. | |
| 8,123,699 B2 | 2/2012 | Lyon | |
| 2003/0050574 A1 | 3/2003 | Krueger | |
| 2003/0139688 A1 | 7/2003 | Lamoureux et al. | |
| 2003/0225364 A1 | 12/2003 | Kraft et al. | |
| 2003/0233114 A1 | 12/2003 | Merboth et al. | |
| 2004/0077973 A1 | 4/2004 | Groenke et al. | |
| 2004/0097828 A1 | 5/2004 | Pellegrino et al. | |
| 2004/0153005 A1 | 8/2004 | Krueger | |
| 2004/0191897 A1 | 9/2004 | Muschler | |
| 2004/0267154 A1 * | 12/2004 | Sutton et al. | 600/562 |
| 2005/0021067 A1 | 1/2005 | Kim | |
| 2005/0209564 A1 | 9/2005 | Bonner et al. | |
| 2006/0167379 A1 | 7/2006 | Miller | |
| 2006/0189996 A1 | 8/2006 | Orbay et al. | |
| 2007/0016100 A1 | 1/2007 | Miller | |
| 2007/0055282 A1 | 3/2007 | Muschler | |
| 2007/0055291 A1 | 3/2007 | Birkmeyer et al. | |
| 2007/0123815 A1 | 5/2007 | Mark | |
| 2007/0179455 A1 * | 8/2007 | Geliebter et al. | 604/272 |
| 2007/0179459 A1 | 8/2007 | Geisler et al. | |
| 2007/0197996 A1 * | 8/2007 | Kraft et al. | 604/500 |
| 2008/0119759 A1 * | 5/2008 | McLain | 600/567 |
| 2009/0149774 A1 | 6/2009 | Simon et al. | |

FOREIGN PATENT DOCUMENTS

| | | |
|---|---|---|
| EP | 2407200 A1 | 1/2012 |
| EP | 2420848 A2 | 2/2012 |
| FR | WO2005/041790 A2 | 10/2004 |
| GB | 2130890 | 11/1983 |
| JP | 2004344299 A | 5/2003 |
| JP | 2005087519 A | 9/2003 |
| JP | 2005087520 A | 9/2003 |
| JP | J132004136106 A | 12/2003 |
| JP | 2005087521 A | 4/2005 |

OTHER PUBLICATIONS

Aspiration of Osteoprogenitor Cells for Augmenting Spinal Fusion: Comparison of Progenitor Cell Concentrations from the Vertebral Body and Iliac Crest by Robert F. McLain et al., The Journal of Bone and Joint Surgery (2005).

Analysis of anatomic morphometry of the pedicles and the safe zone for through-pedicle procedures in the thoracic and lumbar spine by Lien et al., European Spine Journal (2006).

* cited by examiner

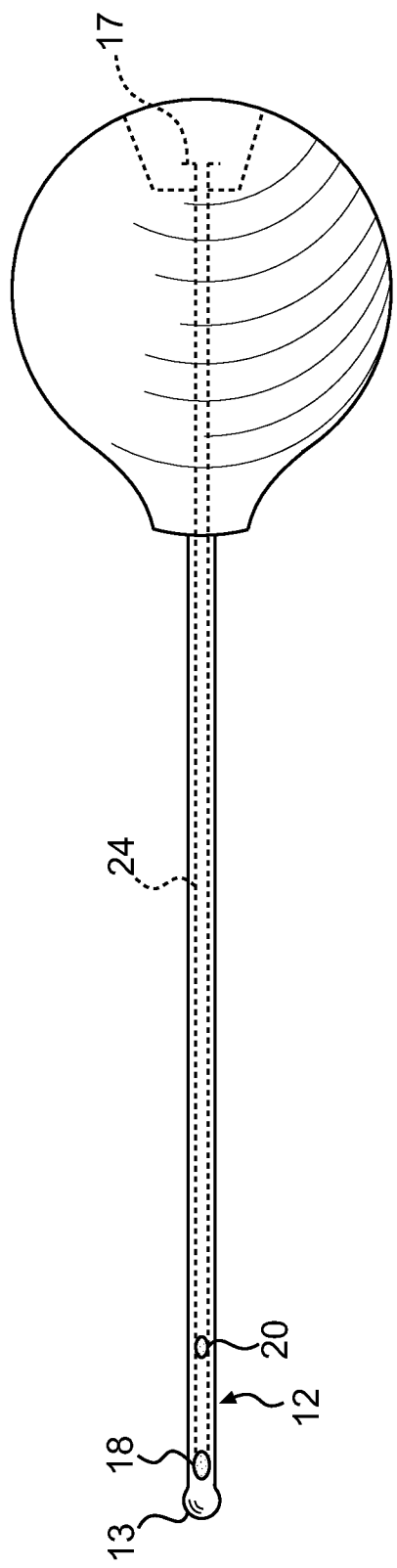
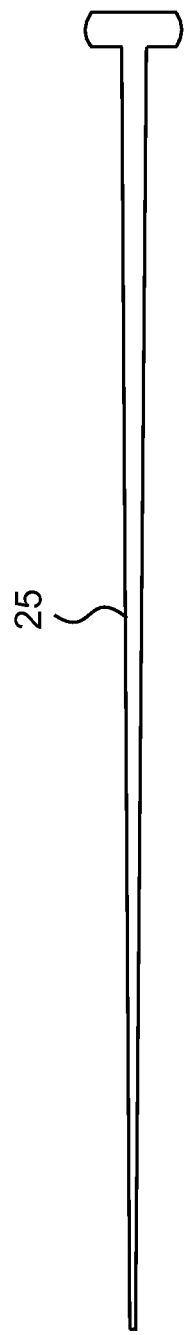
FIG. 4A
FIG. 4B

SPINAL ASPIRATION APPARATUS

BACKGROUND OF THE INVENTION

1. Field of the Invention

The present disclosure relates to an aspiration apparatus and more specifically to an aspiration apparatus for spinal applications.

2. Description of the Related Art

Bone marrow is often used in orthodpaedic procedures to augment fracture healing. It is also an excellent source of mesenchymal stem cells (MSC's) and/or tissue progenitor cells (TPC's). These multi-potent cells have broad applications in addition to orthopaedics and may be used in the fields of cardiology, oncology and other areas. As new techniques are being developed to use these cells and to culture them ex-vivo it has become increasingly important to be able to procure large volumes of highly cellular marrow from the body.

At present, the pelvis is the source for almost all of the marrow that is used for mesenchymal stem cells. Obtaining marrow from the pelvis, however, can be difficult and may present risks to the abdominal cavity, especially when obesity obscures normal landmarks. Additionally, patients undergoing lower extremity procedures such as ankle or tibia fractures often do not have the pelvis readily accessible for sterile bone marrow access. As a result, it is desirable to have the flexibility to harvest marrow from alternative locations.

A further problem is that the aspiration of more than approximately two to four cubic centimeters of marrow in one area has been shown to result in the subsequent withdrawal of local "venous blood" as opposed to marrow and therefore significantly deceases the MSC/TPC count. This requires the frequent relocating of the needle within a given access point into the bone in order to avoid overlapping areas that have already been "tapped out" of marrow. Each additional relocation, however, creates an additional risk for the patient.

The spinal vertebra can also be a source of marrow, but the collection of marrow from the vertebral body has been complicated by the varying structure of the pedicle, the adjacent neural structures and a lack of suitable instruments that can readily access the vertebral body through the pedicle pathway and aspirate a substantial amount of bone marrow without multiple relocations. Current aspiration devices that use traditional needles with a single aperture or multiple parallel radially aligned apertures are limited in the amount of marrow that can be taken before over harvesting and the drawing of substantially venous blood. Relocating the needle within the vertebra, even using the same pedicle pathway, can still result in over harvesting and increases the risk to the patient.

A specialized apparatus is needed for the harvesting of marrow from a vertebra that can readily penetrate through the pedicle pathway and has an arrangement of apertures that are aligned for the harvesting of approximately half of the marrow of a vertebra from a single location without relocating the apparatus.

SUMMARY OF THE INVENTION

A spinal aspiration apparatus is disclosed that is adapted for the harvesting of bone marrow from a vertebra. The spinal aspiration apparatus comprises a needle that includes a distal end portion and a proximal end portion. The distal end portion includes a plurality of apertures and the proximal end portion includes an external interface. The needle defines a lumen that is in fluid communication with the plurality of apertures and the external interface. The distal end portion and proximal end portion define a central longitudinal axis. The distal end portion has tubular walls that include a first side, an opposed second side, a third side and a fourth side. The distal end portion has a distally directed taper that terminates in a solid tip and is adapted to penetrate through a pedicle pathway of a vertebra.

A plurality of apertures is defined in the distal end portion. Each aperture defines an axis and each axis diverges from the other axes of the plurality of apertures. The size and the alignment of each aperture defines each harvest zone and the plurality of apertures defines an array of harvest zones for the harvesting of approximately one-half of the bone marrow from a vertebra from a single location in the vertebra. A handle is connected to the proximal end portion. The external interface is adapted to provide a fluid tight coupling with an external source of reduced pressure.

The first side of the distal end portion includes a plurality of apertures and at least two apertures of the plurality of apertures draw an approximately equivalent first flow rate when an external source of reduced pressure is applied through the external interface. At least one aperture is defined in the second side and the at least one aperture draws a second flow rate when the external source of reduced pressure is applied. The second flow rate is less than the first flow rate. The external source of reduced pressure includes an anti-coagulant. The needle includes a valve that opens and closes the lumen. The needle includes a visible portion that provides visibility within the needle. The handle is at least partially transparent and at least provides visibility into the external source of reduced pressure. Each axis of the at least two apertures defines a separate plane with the longitudinal axis.

The spinal aspiration apparatus has a first position external to a vertebra and a second position wherein the distal end portion of the needle is positioned at a predetermined location in a body of the vertebra. The needle is placed in fluid communication with the external source of reduced pressure and the plurality of diverging apertures define an array of harvest zones that differ in flow rate depending upon the location and angular direction of each aperture on the distal end portion and the predetermined location of the distal end portion in the vertebral body.

The external interface includes a second needle that has a proximally directed penetrating point. The second needle is recessed in a receptacle of the external interface in the handle. The second needle includes a port that is in fluid communication with the lumen of the needle. The receptacle and needle are adapted to interface with a sealed vial that is a source of reduced pressure. The receptacle of the external interface includes a retention mechanism that is adapted to selectively retain the vial in position in the receptacle and release the vial for removal from the receptacle.

A method of aspirating a vertebra is described that comprises the steps of providing an aspiration apparatus that includes a needle that has a distal end portion and a proximal end portion. The distal end portion has a shape for penetrating through a pedicle pathway. The proximal end portion includes an external interface. The needle defines a lumen that is in fluid communication with a plurality of apertures in the distal end portion and the external interface. The external interface is adapted to provide a fluid tight coupling with an external source of reduced pressure. A handle is connected to the proximal end portion. The method includes using the aspiration apparatus for penetrating a pedicle pathway in a vertebra and positioning the distal end portion of the needle at a location in the vertebra. The method also includes introducing an external source of reduced pressure through the external interface for the harvesting of up to approximately one-half of the marrow of the vertebra from a single location within the vertebra. Each of the plurality of apertures has a diverging axis of alignment from the other apertures in the plurality of apertures for the defining of separate harvest areas.

The step of introducing further comprises monitoring the quality of the harvested marrow through a portion of the needle. The method can further comprise controlling the application of the source of reduced pressure using a valve connected to a lumen of the needle. The step of using can further comprise finding the pedicle pathway. The step of introducing can further include drawing approximately one-half of the marrow from the vertebra using a first pedicle pathway, securing the valve and penetrating a second pedicle pathway. The step of introducing can include estimating the volume of marrow in one-half of the vertebra and using markings on the external source of reduced pressure to preclude the over harvesting of marrow.

BRIEF DESCRIPTION OF THE DRAWINGS

Preferred embodiments of the disclosure are described below with reference to the drawings, wherein like numerals are used to refer to the same or similar elements.

FIG. 4A is a side view of a second embodiment of the spinal aspiration apparatus of FIG. 1 that includes a bulbous distal end;

FIG. 4B is view of a stylet that can be employed with the spinal aspiration apparatus of FIG. 4A;

DETAILED DESCRIPTION OF THE INVENTION

Figure 1:
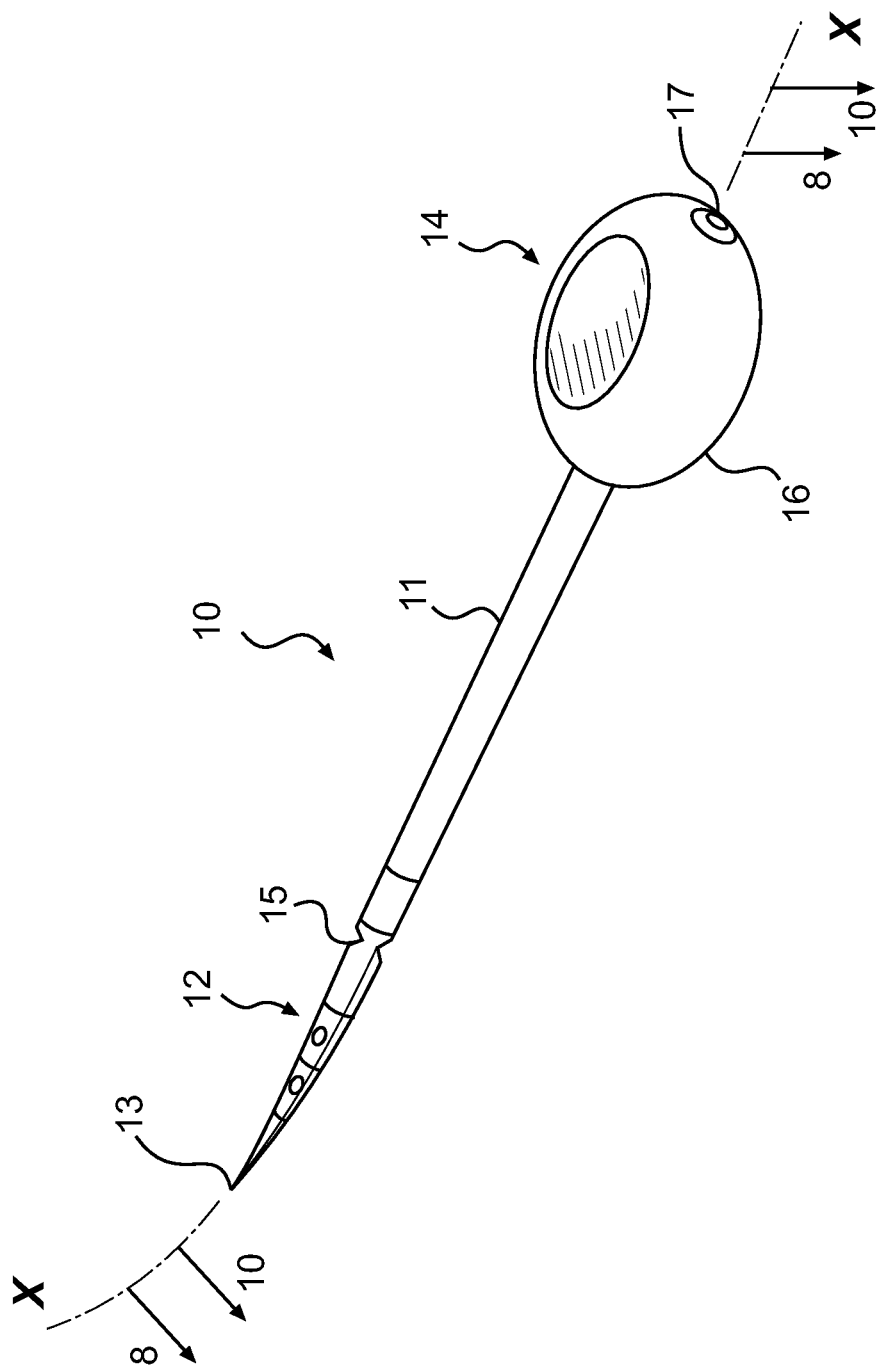
FIG. 1 is a proximal and side perspective view of the spinal aspiration apparatus constructed in accordance with the present disclosure.

Referring initially to FIG. 1, a spinal aspiration apparatus 10 includes a needle 11 that extends between a distal end portion 12 and a proximal end portion 14. Distal end portion 12 includes a tip or distal end 13. Proximal end portion 14 includes a handle 16 and an external interface 17. Distal end portion 12 includes a plurality of apertures that is in fluid communication with external interface 17. Aspiration apparatus 10 defines a central longitudinal axis-X that extends along the length of needle 11 between distal end 13 and proximal end portion 14.

Needle 11 has a shaft that extends between the proximal end of distal end portion 12 and external interface 17. In this preferred embodiment, the shaft is straight and has a cylindrical outer surface. Distal end portion 12 and the shaft of needle 11 can selectively include markings that indicate the depth of penetration of aspiration apparatus 10. A reduced diameter neck 15 separates the proximal end of distal end portion 12 and the shaft.

Figure 2:
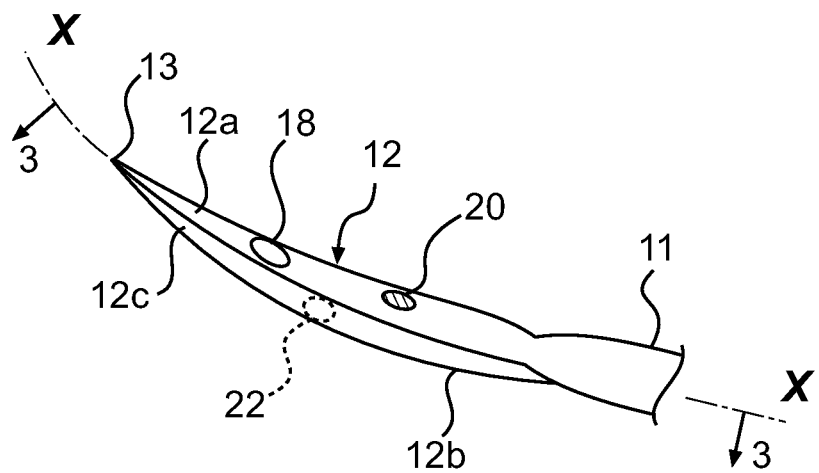
FIG. 2 is a close-up perspective view of a first side and a third side of a distal end portion of the spinal aspiration apparatus of FIG. 1.
Figure 9:
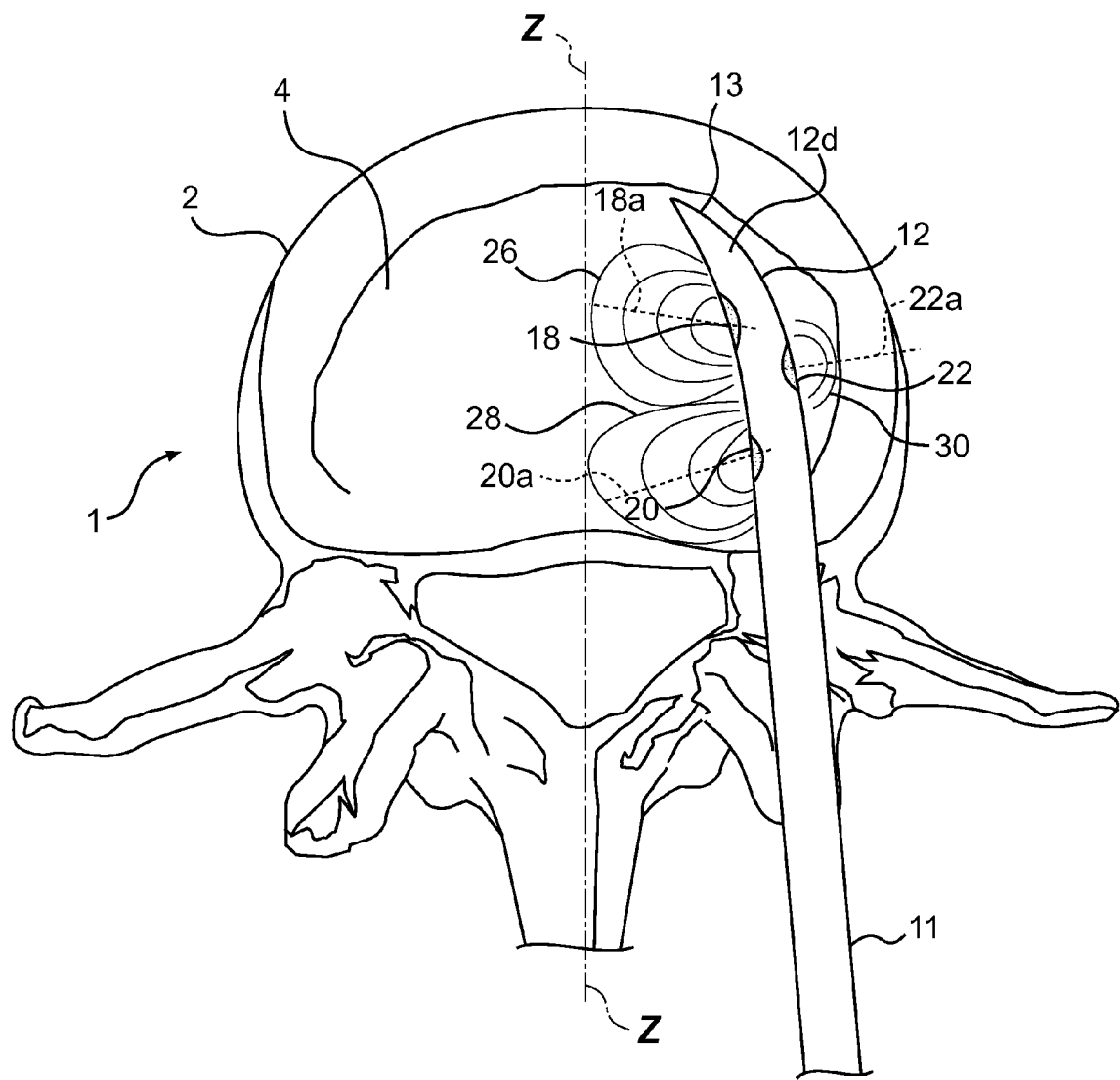
FIG. 9 is a close-up top view of the vertebra of FIG. 8 and an idealized side view of the distal end portion of the aspiration apparatus of FIG. 8 showing the bone marrow harvesting region in the vertebra.
Figure 11:
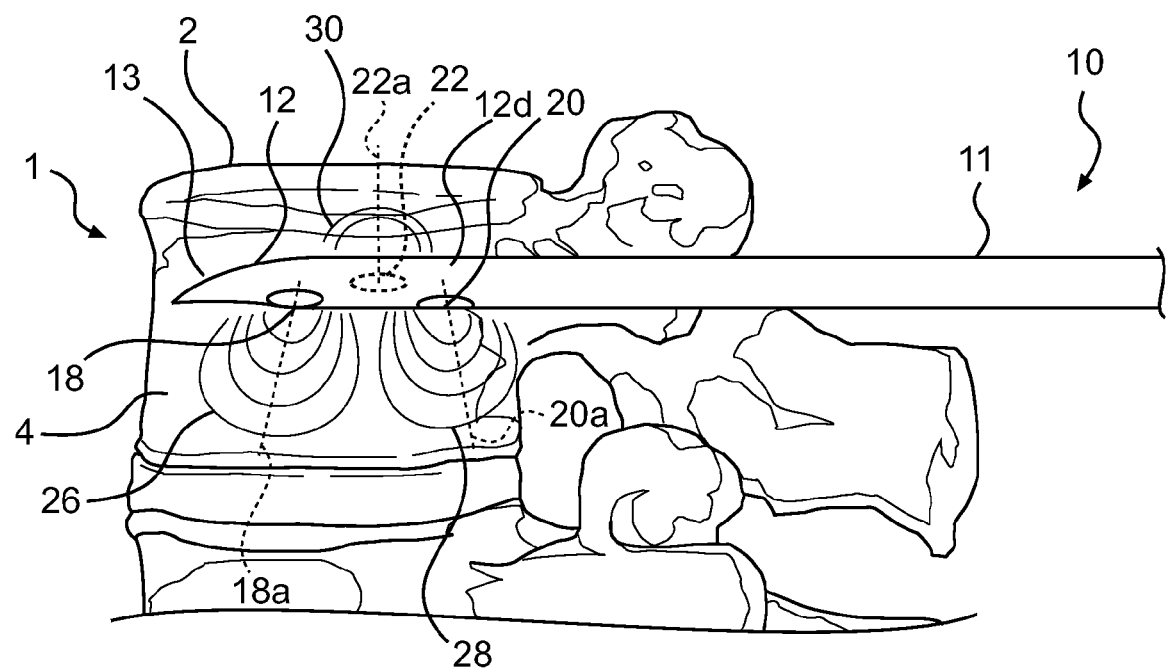
FIG. 11 is a close-up side view of the vertebra partially cut away of FIG. 10 and a perspective view of an idealized outline of the spinal aspiration apparatus of FIG. 10 showing the harvesting region in the vertebra.

As shown in FIG. 2, distal end portion 12 of needle 11 preferably includes a first side 12a, a second side 12b, a third side 12c and a fourth side 12d (see FIGS. 9 and 11). Distal end portion 12 is preferably a four-sided angular structure that includes a taper to distal end 13. The angular tapered arcuate shape of distal end portion 12 is similar to that of pedicle finding instruments. Distal end 13 is a solid terminal end of needle 11 that includes a tip structured for pedicle finding applications.

First side 12a is directed radially inward towards the center of the arcuate shape of distal end portion 12. Second side 12b is directed radially outward from the center of the arcuate shape of distal end portion 12 and opposes first side 12a and. First side 12a and second side 12b are connected by third side 12c and fourth side 12d to form the tubular walls of distal end portion 12.

Figure 3:
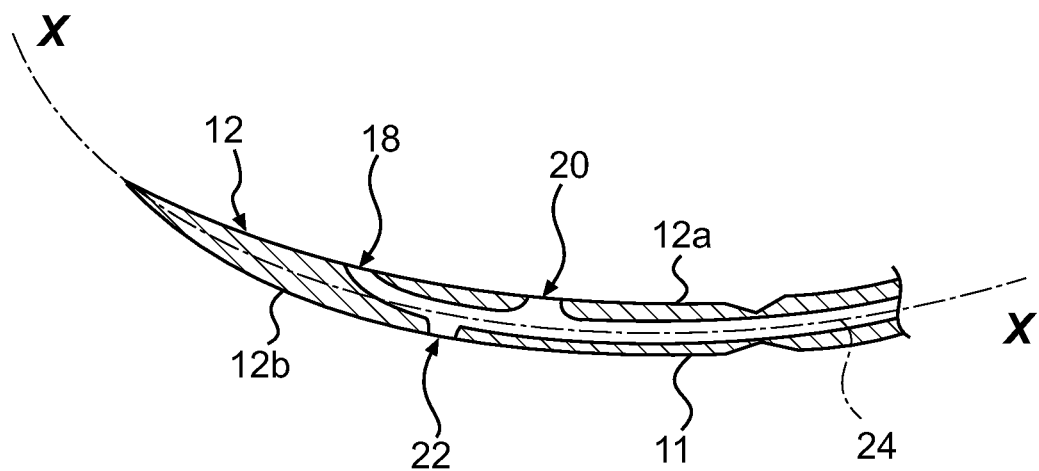
FIG. 3 is a cross-sectional view of the distal end portion of the spinal aspiration apparatus of FIG. 2 taken along lines 3-3.

Referring now to FIGS. 2 and 3, in this preferred embodiment, at least two apertures 18 and 20 is a plurality of apertures that are defined in first side 12a and at least one aperture is defined in second side 12b. Sides 12a, 12b, 12c and 12d are tubular walls that define a lumen 24 in distal end portion 12 of needle 11. Apertures, 18, 20 and 22 are through holes in the tubular wall of distal end portion 12 that are in fluid communication with lumen 24. The tubular wall of needle 11 and lumen 24 extends between distal most aperture 18 and external interface 17.

The at least two apertures 18 and 20 as well as at least one aperture 22 have directional alignments that diverge from one another. The alignment of each of the at least two apertures 18 and 20 preferably defines a separate plane with the longitudinal axis-X. It is understood that the at least two apertures 18 and 20 as described herein can include an array of apertures that extends across two or more of first side 12a, third side 12c and fourth side 12d that have diverging alignments relative to each other and to at least one aperture 22 in second side 12b.

In addition, the cross-sectional areas of two or more of the at least two apertures 18 and 20 can be varied to define a predetermined rate of laminar fluid flow when a level of reduced pressure is applied through external interface 17 by an external source of reduced pressure. In one preferred embodiment, apertures 18 and 20 are circular apertures and fluid mechanics are employed to vary the diameter of distal aperture 18 relative to the diameter of proximal aperture 20 such that at least two apertures 18 and 20 of the plurality of apertures on side 12a draw an approximately equivalent flow rate.

The cross-sectional dimensions of at least two apertures 18 and 20 as well as the flow rates through apertures 18 and 20 are calculated using fluid mechanics to account for the flow through at least one aperture 22 in second side 12b into lumen 24. In this preferred embodiment, the diameter of the through hole of at least one aperture 22 is less than the diameter of apertures 18 and 20 and draws a reduced flow rate than apertures 18 and 20. At least one aperture 22 has a cross-sectional area for a predetermined rate of laminar fluid flow when connected to the external source of reduced pressure that is less than the individual fluid flows of apertures 18 and 20.

At least one aperture 22 has an alignment that diverges from any additional apertures in second side 12b and in this one preferred embodiment aperture 22 has an alignment that is approximately perpendicular to the longitudinal axis. The cross-sectional size of the through hole of at least one aperture 22 in second side 12b can vary in any manner and does not necessarily produce an equivalent flow rate as any additional apertures in side 12b.

It is understood that each aperture of the plurality of apertures in distal end portion 12 defines a centerline or an axis that defines the alignment of that aperture. The cross-sectional area of any one of the plurality of apertures as defined herein is a cross-section perpendicular to the axis defined by that aperture. This is independent of the shape of the cross-section of the aperture.

In one preferred embodiment, apertures 18, 20 and 22 are approximately aligned with the longitudinal axis to define a single plane. At least one aperture 22 is positioned approximately midway between apertures 18 and 20 in opposing side 12b. It is understood that additional apertures 18, 20 and 22 can be positioned on their respective sides. Further, apertures can also be selectively included in sides 12c and 12d.

As shown in FIGS. 1 and 3, handle 16 preferably has a shape that approximates a spherical ball. Handle 16 can include a position indicator for aspiration apparatus 10, such as a flattened portion 19 that provides a tactile indication of the orientation of arcuate distal end portion 12. Alternative indicators can include one or more undulations of the surface of the handle 16 as well other tactile or sensory-based distinctions.

External interface 17 is approximately aligned with or slightly recessed below the surface of handle 16 and is adapted to provide a fluid tight connection with an external source of reduced pressure. In this preferred embodiment, external interface 17 is a leur lock that provides a fluid tight coupling with a mating leur lock syringe. The syringe can also be employed as an external source of reduced pressure.

Referring now to FIG. 4A a second preferred embodiment of spinal aspiration apparatus 10 includes a needle 11 that has a tapered approximately conical shaped distal end portion 12 that can further include a bulbous tip 13. As defined herein the conical shaped distal end portion 12 includes arcuate first side or tubular wall 12a as well as an arcuate second side, arcuate third side and arcuate fourth side. At least two apertures are defined in first side 12a and at least one aperture 22 is defined in second side 12b.

In this preferred embodiment, distal end portion 12 includes at least two apertures 18 and 20 in first side 12a and at least one aperture 22 in side 12b as described previously. In this preferred embodiment, distal end portion 12 can have a straight tapered shape, but preferably has an at least partially arcuate tapered shape.

The proximal end portion of handle 16 includes an aperture or recess that positions external interface 17 below the outer surface of handle 16. The recess of external interface 17 below the surface of handle 16 advantageously provides a predetermined degree of structural support for the external source of reduced pressure during operational use and can include a port that is a window or a slot that provides visibility into the external source of reduced pressure and markings that define volume levels.

As shown in FIGS. 4A and 4B, spinal aspiration apparatus 10 can also include a stylet 25 that is selectively employed to purge or clean lumen 24. Stylet 25 can be rigid and straight or alternatively flexible along its longitudinal axis such that the distal end portion of stylet 25 can flex and accommodate arcuate distal end portion 12 and passage through apertures 18, 20 and 22.

Figure 5:
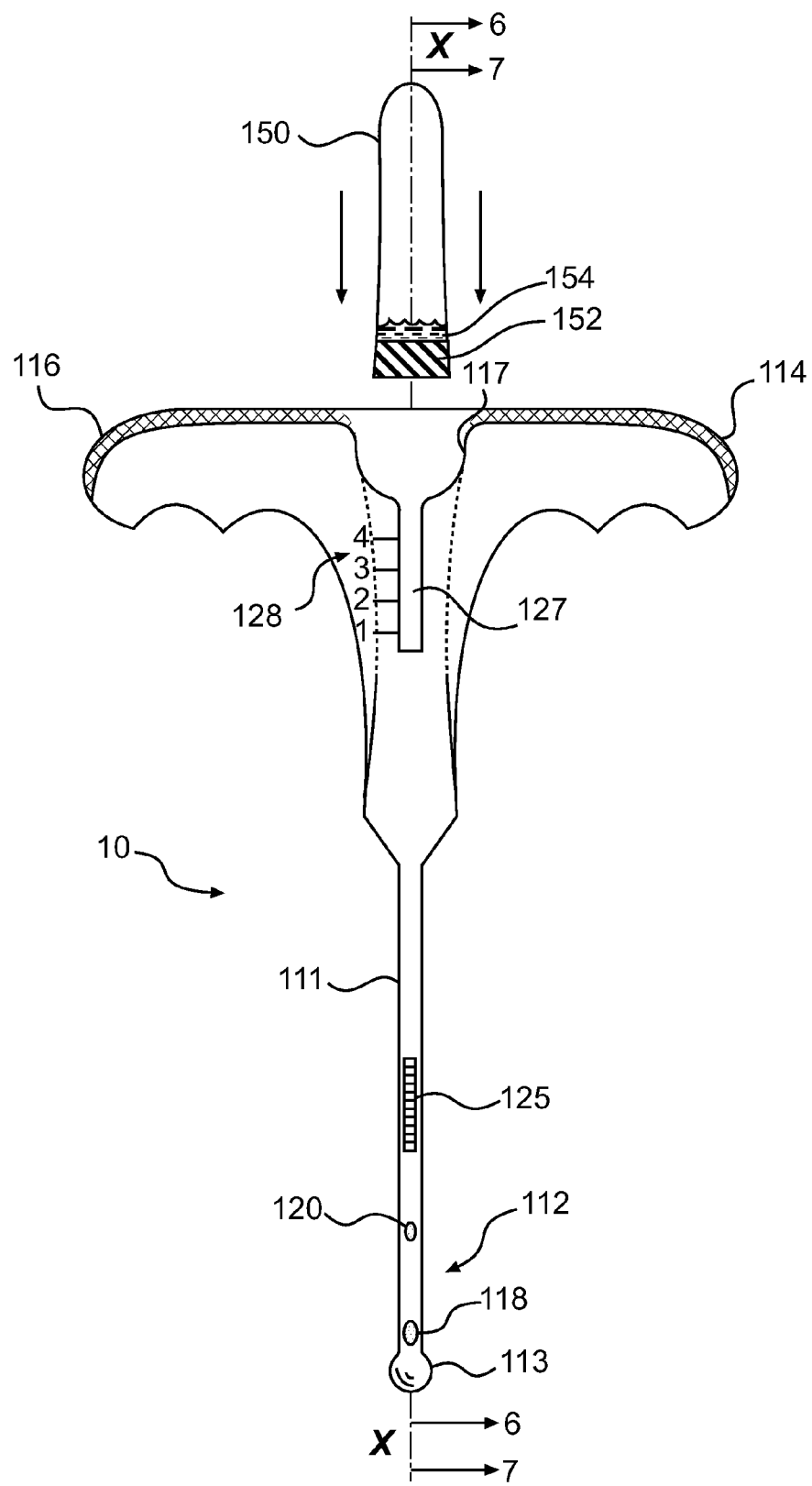
FIG. 5 is a side view of a third embodiment of the spinal aspiration apparatus of FIG. 1 that includes an external interface in a proximal end portion of the spinal aspiration apparatus, the external interface adapted to receive a vial.

As shown in FIG. 5, a third preferred embodiment of spinal aspiration apparatus 10 includes a needle 111 with a distal end portion 112 and a proximal end portion 114. Distal end portion 112 includes a distal end or tip 113. Proximal end portion 114 includes a handle 116 and an external interface 117.

Needle 111 has a bulbous tip 113 that aids in precluding undesirable penetrations during surgical procedures and is suitably sized for penetration through the pedicle pathway. Needle 111 can also include markings or graduations 125 on the external surface that indicate the depth of penetration. Needle 111 can be an approximately rigid structure or alternatively have a structure with a controlled amount of flexibility along the longitudinal axis-X. Needle 111 retains the ability to sustain fluid flow during flexing.

Handle 116 has a "T" shape in this preferred embodiment that includes a window 127 that can be a cutout in handle 116 or a transparent or translucent portion and markings 128 associated with window 127. Alternatively, handle 116 can be transparent or translucent such that exterior interface 117 is readily visible through handle 116.

External interface 117 defines an aperture or receptacle in handle 116 that is adapted to receive a standard size sealed vial 150. In this preferred embodiment, vial 150 is a clear glass or clear polymer that is sealed by a cap 152 to retain a reduced pressure or pressure below that of the atmosphere such that a desired level of low pressure force is provided through apertures 18, 20 and 22 and lumen 124. Vial 150 can also selectively include an anti-clotting liquid 154.

Figure 6:
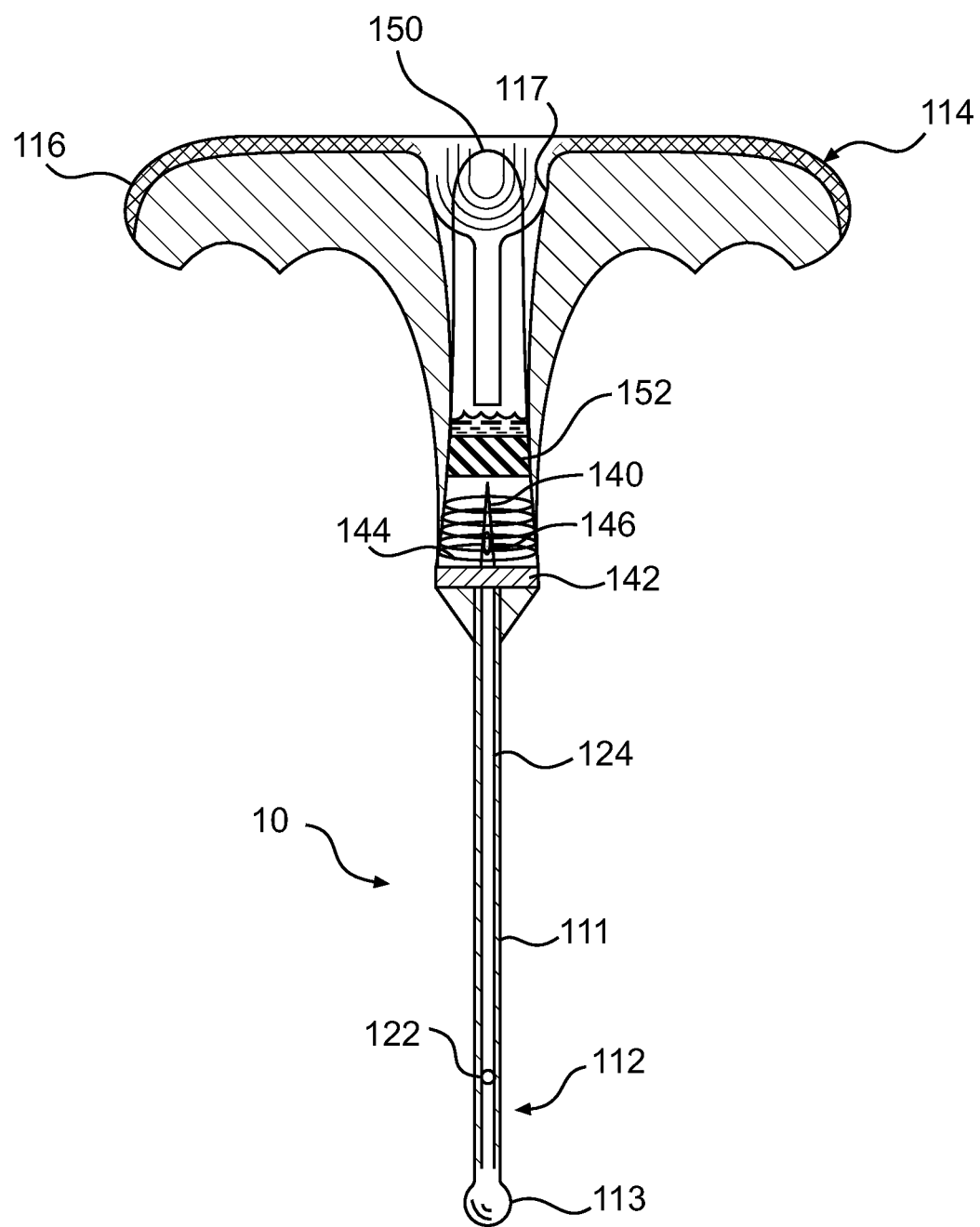
FIG. 6 is a cross-sectional view of the spinal aspiration apparatus of FIG. 5 taken along lines 6-6 that shows the vial partially positioned in a receptacle of the external interface.

Referring now to FIG. 6, external interface 117 includes a needle 140, a receptacle that has at least one sidewall, a terminal end 142 and a bias member 144. External interface 117 in this preferred embodiment includes a longitudinally aligned receptacle that is defined by the at least one sidewall and terminal end 142. Needle 140 is a longitudinally aligned tube with a penetrating proximally directed tip that extends through terminal end 142 and is in fluid communication with lumen 124. Bias member 144 is preferably connected to the proximal side of terminal end 142. Needle 140 defines a lumen and a proximal end portion that includes a port 146.

Needle 11 can also include a shut off valve 148 that can be operated to selectively open and close fluid communication between lumen 124 and needle 140. Valve 148 can be positioned directly on shaft 11 or handle 16. Alternative valves 148 include a biased enclosure of needle 140 that is opened by the application of a reduced pressure such as that of vial 150.

In one preferred embodiment, the proximal end of needle 111 includes a portion that provides visibility into needle 111 such as a window or a clear tubular extension that is located within handle 116. The visible portion of needle 111 can also include valve 148 and/or external interface 117. Handle 116 provides visibility into the visible portion using a slot or window. The visible portion can be made of any clear material suitable for medical applications such as a polymer or glass based material. In one preferred embodiment, handle 116 is also made of the same material as the visible portion.

Figure 7:
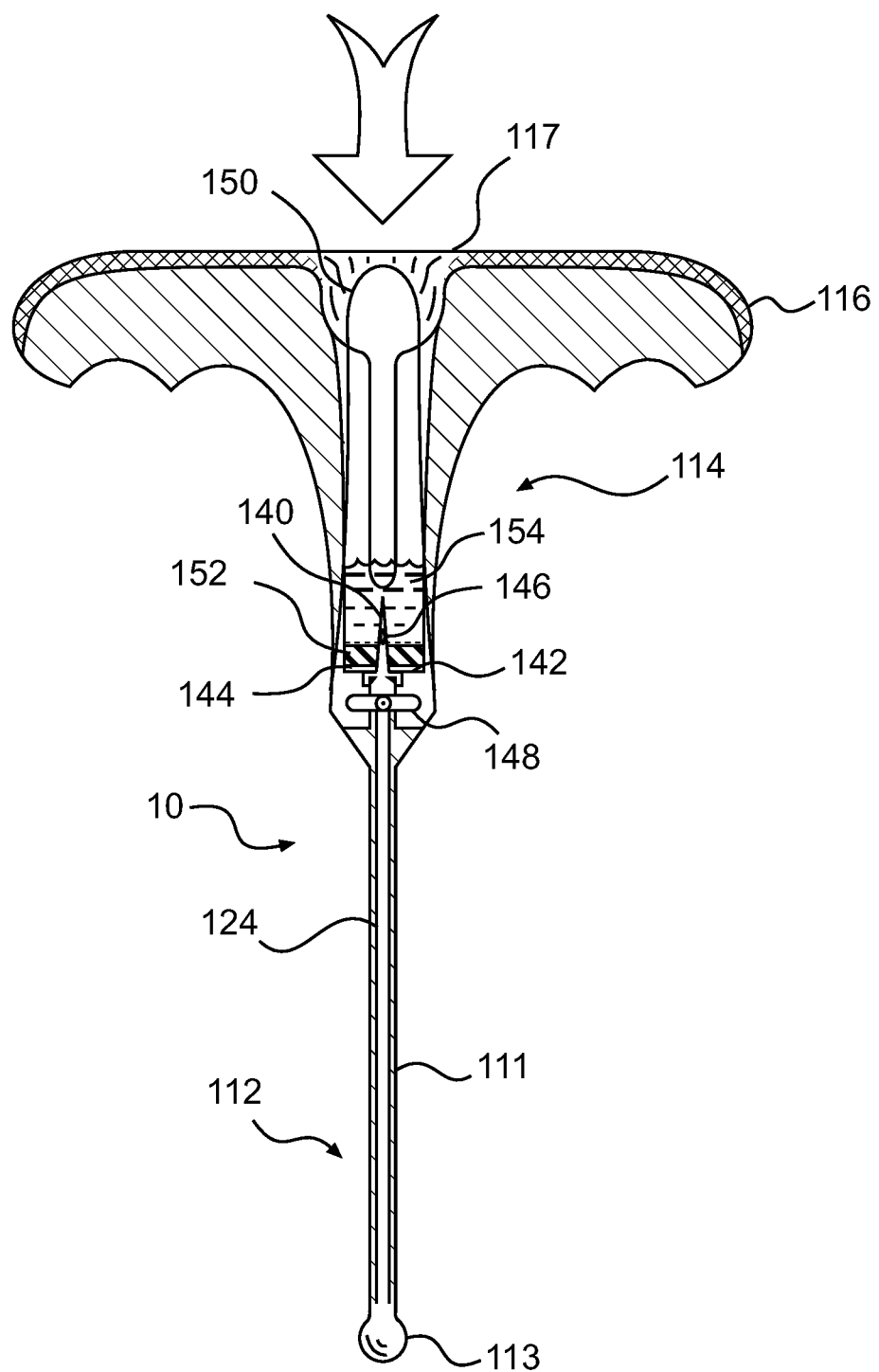
FIG. 7 is a cross-sectional view of the spinal aspiration apparatus of FIG. 5 taken along lines 7-7 that shows the vial fully emplaced in the receptacle and coupled to a lumen of the spinal aspiration apparatus.

As shown in FIG. 7, vial 150 is pushed distally into the aperture defined by external interface 117 and against the bias of bias member 144. Vial 150 is secured in place by a retention mechanism associated with the receptacle of external interface 117. The mechanism could be, for example, a friction fit or a snap type interface fit between the sidewalls and vial 150. An external release switch can be selectively positioned on the outside of handle 116 with the actuation of the switch releasing the mechanism that secures vial 150 in the receptacle of external interface 117. Bias member 144 then urges vial 150 from the receptacle. When vial 150 is fully inserted into the receptacle of external interface 117, vial 150 is preferably substantially recessed in handle 116 and needle 140 penetrates through seal 152 such that aperture 146 and the interior of vial 150 are in fluid communication with lumen 124.

It is also understood that alternative arrangements for the positioning and removal of vial 150 can have different structures and retention mechanisms. In particular, direct manual access can be provided to the vial through additional apertures in handle 116 as well as the use of an external device for the gripping and removal of vial 150 from handle 116. Similarly the structure described herein for handle 116 can be readily employed with handle 16 of the first embodiment such that the approximately spherical or bulbous shape of handle 16 that can at least partially recess vial 150. Further modifications can include providing an external interface 17 that has a recess, window 127, markings 125, 128 and needle 146 while accommodating the desired feel and manual dexterity association with the traditional external structure of a pedicle finder. Similarly, the third embodiment of aspiration apparatus 10 can include a leur lock with a recessed or surface external interface 17.

Referring now to FIGS. 1 and 5, the materials of construction of spinal aspiration apparatus 10 can vary depending upon the intended use. For example, in one preferred embodiment, handle 16 is constructed of wood, but it is understood that handles 16 and 116 can be fabricated of any suitable materials as defined herein for medical applications to include metals, polymers and composites. Similarly, needle 11 is preferably made of steel suitable for surgical applications, but it is understood that alternative materials such as polymers and composites can be utilized that have the appropriate strength for spinal applications.

Figure 8:
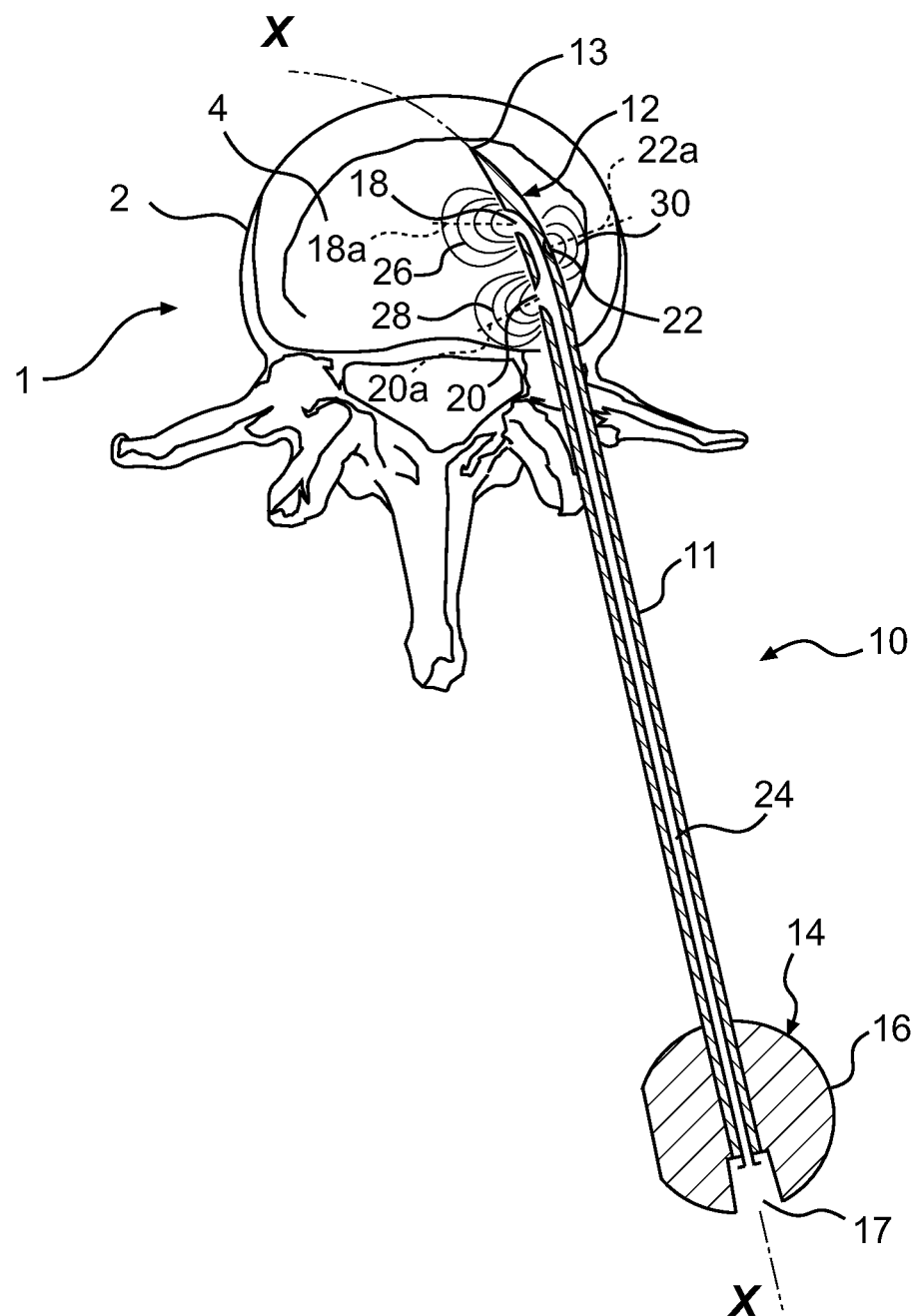
FIG. 8 is a top view of a vertebra with a cross-sectional side view of the spinal aspiration apparatus of FIG. 1 taken along lines 8-8 located therein showing a bone marrow harvesting region in the vertebra.

In operation, as shown in FIGS. 1, 8 and 9 spinal aspiration apparatus 10 is employed during a surgical procedure on a patient through an incision in proximity to a vertebra 1. The pedicle pathway of vertebra 1 is located and the angled arcuate shape of distal end portion 12 of spinal aspiration apparatus 10 can advantageously pass through the pedicle pathway, cancellous bone and anterior cortex of a vertebral body 2 that contains marrow 4. The location and angular direction of distal end portion 12 in body 2 can be verified by contacting distal tip 13 with the anterior of vertebra 1 and markings (see FIG. 1 and FIG. 5) on needle 11. Alternatively or in addition, the location and angular direction of distal end portion 12 can be verified by external imaging means such as ultrasound, MRI or CT scans, for example. As shown in this preferred embodiment, the representative diverging alignment of apertures 18, 20 and 22 of distal end portion 12 direct and align the corresponding harvest zones 26, 28 and 30 such that the harvest zones encompass approximately half of vertebra 1.

An external source of reduced pressure, such as a syringe with a leur lock interface, is coupled to the leur lock of exterior interface 17 before or after the entry of aspiration apparatus 10 into the pedicle pathway. The syringe can optionally include a liquid such as an anti-coagulant. The spinal aspiration apparatus is then used to locate the pedicle pathway using distal tip 13. The markings on needle 11 can be used to gauge and selectively control the depth of penetration of needle 11 into vertebra 1.

Aperture 18 defines a central axis 18a, aperture 20 defines a central axis 20a and aperture 22 defines a central axis 22a. Each of axes, 18a, 20a, and 22a diverges from the other axes. The quantity, arrangement, cross-sectional area and directional alignment of the plurality of apertures in distal end portion 12 is structured to define an array of harvest zones that aspirate approximately one-half of marrow 4 from a single positional location in vertebral body 2. The directional alignment of the apertures relative to the longitudinal axis can vary from a proximal to a distal orientation depending upon the location of the aperture on distal end portion and the positional location of distal end portion 12 in body 2. In one preferred embodiment, the plurality of apertures has an oblique distal angular direction relative to the longitudinal axis. Oblique as defined herein is transverse and non-perpendicular to the longitudinal axis.

The diverging alignment of axes 18a and 20a takes into account factors such as the preferred positioning of distal end portion 12 in body 2, the morphology of vertebra 1 and the arcuate shape of distal end portion 12. In one preferred embodiment, the preferred angular position of shaft 11 relative to a sagittal plane is an acute angle that preferably approaches an approximate alignment with the sagittal plane. The shape of neck 15 of needle 11 can also accommodate an increased ability to select a particular location and angular position of distal end portion 12 of aspiration apparatus 10 in the vertebral body 2. It is understood, however, that the morphology of the pedicle pathway relative to body 2 can vary in both the sagittal plane and transverse plane in vertebra 1 depending upon the location of vertebra 1 in the spinal column and other factors. In this regard, the preferred alignment of the distal end portion 12 in vertebral body 2 can vary relative to the sagittal plane with alternative diverging alignments, arrangements and cross-sectional areas of the plurality of apertures of distal end portion 12.

The preferred position of distal end portion 12 in body 2 also includes directing side 12a with diverging axes 18a and 20a of at least two apertures 18 and 20 approximately medially towards a midsagittal plane and axis 22a approximately laterally outwardly. The representative diverging alignments of axes 18a, 20a and 22a defines the axes of harvest zones 26, 28 and 30, respectively. As noted previously, at least two apertures 18 and 20 can include additional apertures in third side 12c and fourth side 12d that are define a three-dimensional array of diverging apertures. It is understood that the number of diverging apertures in distal end portion 12 are shown in a representative manner in the figures and the quantity and location of the apertures can vary depending upon factors such as those described above.

Once spinal distal end portion 12 is positioned at the predetermined location in body 2, marrow 4 is collected using the syringe to create a source of reduced pressure and harvest marrow 4 through at least two apertures 18 and 20, at least one aperture 22, lumen 24 and into the syringe. The size of each aperture in distal end portion 12 is selected to control the flow rate of marrow and size of each individual harvest area. For example, the flow rate of at least one aperture 22 is less than the flow rate of at least two apertures 18 and 20 due to the smaller volume of marrow 4 in proximity to side 12b and the substantial volume of marrow 4 in proximity to side 12a. The flow rate through each aperture in distal end portion 12 and lumen 24 can be calculated using standard fluid mechanics techniques for incompressible fluid flow such as those of Navier-Stokes and Hagen-Poiseuille equations as well as Bernouli's principle. The predetermined location in body 2 is defined herein as a preferred approximate location in body 2 that can be determined by markings on needle 11, the angular position of needle 11 relative to the mid sagittal plane and/or external imaging sources.

The flow rate and shape of harvest zones can also be tailored by the shape of the rim of the apertures and shape of the tubular walls that define the apertures. For example, the breadth or lateral width of a given harvest volume can be expanded by increasing the taper of the tubular walls of the rim of the aperture to create a conical taper that increases the lateral breadth of the harvest area. The size of the desired harvest volume from at least two apertures 18, 20 and at least one aperture 22 is systematically calculated as described above for laminar flow of an incompressible fluid such as bone marrow.

The unique diverging alignment of apertures 18 and 20 of first side 12a in conjunction with the diverging alignment of aperture 22 of second side 12b harvests approximately half of the marrow in body 2 from a single location. Harvest volumes 26, 28 and 30 approximately encompass one-half of the marrow of vertebra 1 as shown by the midsagittal aligned axis-Z that approximately divides vertebra 1 in half This advantageously precludes the need to take a first volume of marrow relocate the aspiration apparatus and then repeat the relocation process for the additional collection of marrow in body 2 in order to preclude over harvesting.

The three-dimensional harvest volumes 26, 28 and 30 of aspiration apparatus 10 are advantageously arranged at diverging angles to preclude overlapping within the vertebra. The harvesting of marrow 4 is monitored for quality by viewing through the syringe or alternatively through handle 16. The harvesting process can be stopped by the ceasing of the withdrawal of the syringe plunger or alternatively by the use of a valve 148 and the coupling of a new syringe.

In one preferred embodiment at least two of the at least two apertures 18 and 20 in first side 12a are opposed to an approximately equivalent volume of marrow 4 and have apertures with cross-sectional areas that are sized to provide approximately equivalent flow rates. In another preferred embodiment, the over harvesting of marrow 4 is prevented using estimated volumes of marrow 4 and volume markings on the external source of reduced pressure and/or proximal end portion 14, such as markings 128 of window 127 (See FIG. 5).

In another preferred embodiment, the over harvesting of marrow 4 can be prevented using calculated or predicted estimations of the volumes of marrow 4. The flow rates of individual apertures of the plurality of apertures in distal end portion 12 are calculated using the principles of fluid mechanics such that the apertures directed towards lesser amounts of marrow 4 have a slower flow rate than the apertures directed towards substantial amounts of marrow 4. The marrow 4 of approximately one-half of vertebral body 2 is thus drawn at an overall uniform rate relative to the volume of marrow in proximity to that aperture. The marrow in approximately one-half of the body 2 is harvested by the application of a specified level of reduced pressure until the desired harvest volume is achieved or a predetermined time expires. The volume of marrow 4 in vertebral body 2 to be harvested for a particular application of aspiration apparatus 10 and the flow rate of each aperture of the plurality of apertures of distal end portion 12 is calculated for a given application of reduced pressure by the external source of reduced pressure. The above methods can be used separately or in combination to prevent the drawing of substantial amounts of venous blood.

Once approximately one-half of the volume of the marrow of vertebral body 2 is harvested, the drawing of marrow 4 can be terminated and aspiration apparatus 10 withdrawn from vertebra 1 before a substantial flow of venous blood from one-half of body 2 is harvested. The above volume based and visual methods can be used separately or in combination to prevent the drawing of substantial amounts of venous blood.

Figure 10:
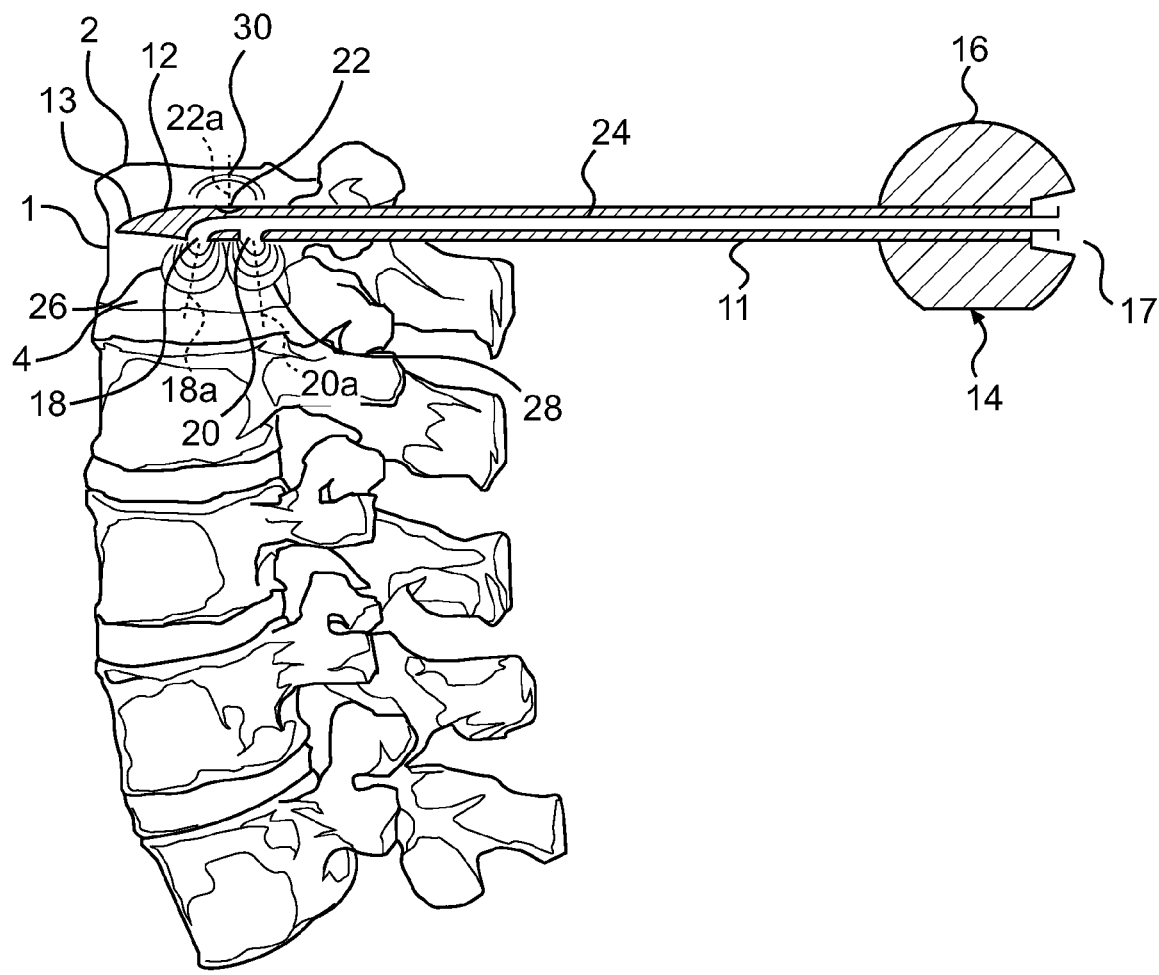
FIG. 10 is a side view of a portion of a vertebral column with a vertebra partially cut away showing a cross sectional side view of the spinal aspiration apparatus of FIG. 1 taken along lines 10-10 showing the bone marrow harvesting region of the aspiration apparatus in the vertebra.

Referring now to FIGS. 10 and 11, once distal end portion 12 of spinal aspiration apparatus 10 is positioned at the desired location in body 2, aspiration apparatus 10 can be rotated at the same location to reorient apertures 18, 20 and 22 to harvest marrow from a different angular area of vertebra 1 such as an approximately sagittal orientation as shown. This option is particularly advantageously when the arrangement of the plurality of apertures on distal end portion 12 and corresponding harvest zones have an approximately planar opposed alignment with sides 12a and 12b.

Referring now to FIGS. 4A, 4B, 5 and 8, the second and third embodiments of aspiration apparatus 10 can be initially employed through a pre-existing incision as described previously with a reduced sized bulbous tip 13 as a pedicle finder and with a larger bulbous tip 13 in the pedicle pathway established by a separate pedicle finder instrument. The second and third embodiments of aspiration apparatus 10 have an improved ability to be employed as a probe to verify the preferred location and angular direction of distal end portion 12 in vertebral body 12. Bulbous tip 13 and markings 125 provide one preferred means for identifying the location and angular direction of the distal end portion 12 of aspiration apparatus 10 in vertebral body 2.

Recessed external interface 17 in handle 16 of the second embodiment of aspiration apparatus 10 advantageously stabilizes and protects the engagement of the external source of reduced pressure with aspiration apparatus 10. Stylet 25 can be used to purge material from lumen 24 and apertures 18, 20 and 22 between or at the conclusion of the application of aspiration apparatus 10.

As shown in FIGS. 5-7 and 11, the third preferred embodiment of spinal aspiration apparatus 10 in operation includes, placing vial 150 from a first and separate position to a second position coupled with lumen 124 by positioning vial 150 into the aperture defined by external interface 117. The positioning of vial 150 in the second position can be done before or after the penetration of distal end portion 112 through the pedicle of vertebra 1. Valve 148 provides functions that include the ability for a user to selectively control the application of reduced pressure from the external source of reduced pressure such as vial 150. Once distal end portion 112 is positioned in body 2, the reduced pressure is initiated by directly connecting vial 150 with needle 140 and/or moving valve 148 to fluidly couple lumen 124 and vial 150.

The drawing of marrow 4 is monitored for quality, the quantity of marrow harvested and/or over harvesting by viewing through window 127, markings 128 of handle 116 and/or into the external source of reduced pressure such as vial 150. This monitoring allows for the viewing of the harvested marrow so as to identify the undesirable over harvesting of marrow 4. Valve 148 can also be employed to secure lumen 124, withdraw a vial 150 and then position a second vial 150 into external interface 17. Each cap 152 of vial 150 provides an interface that automatically re-seals the contents of vial 150 once vial 150 is withdrawn from needle 140. Thus, valve 148 provides the ability to employ multiple vials 150 in sequence with each vial 150 providing its own source of reduced pressure. Each vial 150 can be released using the external release switch or alternatively by directly grasping and removing vial 150. Bias member 144 urges vial 150 from the receptacle of external interface 117 for ease of grasping. When the desired quantity of marrow 4 is harvested or the harvesting is completed, valve 148 can be selectively closed and aspiration apparatus 10 is withdrawn from the patient. The volume based limits described above can also be used separately or in conjunction other forms of monitoring for the quality control of the harvest of marrow 4.

In the preceding specification, the present disclosure has been described with reference to specific exemplary embodiments thereof. It will be evident, however, that various modifications, combinations and changes may be made thereto without departing from the broader spirit and scope of the invention as set forth in the claims that follow. For example, the preferred leur lock external interface 17 of the first embodiment can include a receptacle and/or a vial 150 or an alternative coupling device for an external source of reduced pressure. Thus, the embodiments described herein can be applied or combined as novel features between the embodiments described herein. The drawings and specification are accordingly to be regarded in an illustrative manner rather than a restrictive sense.

What is claimed is:

1. A spinal aspiration apparatus adapted for the harvesting of bone marrow from a vertebra, the spinal aspiration apparatus comprises:
   a tubular needle that includes a distal end portion and a proximal end portion that are connected by a shaft, the proximal end portion includes an external interface, the needle defines a lumen that is in fluid communication with the external interface, the distal end portion, shaft and proximal end portion define a longitudinal axis, the distal end portion has a tubular wall that includes a first side, an opposed second side, a third side and a fourth side, the distal end portion has angular arcuate shape, the first side is directed radially inwardly towards the center of the arcuate shape of the distal end portion and the second side is directed radially outwardly from the center of the arcuate shape of the distal end portion, the distal end portion has a distally directed taper that terminates in a solid tip and is adapted to penetrate through a pedicle pathway to a vertebra;
   a plurality of apertures defined in the distal end portion, the plurality of apertures in fluid communication with the lumen, at least two apertures of the plurality of apertures defined on one of the sides of the distal end portion, the at least two apertures have an approximately equivalent flow rate, the at least two apertures on one of the sides of the distal end portion have directional orientations that include one aperture with a proximal orientation and one aperture with a distal orientation, the at least two apertures on one of the sides of the distal end portion have directional alignments that are in different planes and oblique to the longitudinal axis, the first side includes the at least two apertures with directional alignments that diverge from one another and the second side includes at least one aperture, the size of each aperture of the at least two apertures on the first side of the distal end portion is varied to define approximately equivalent flow rates, the at least two apertures on the first side are positioned approximately in alignment with the longitudinal axis, the at least one aperture is positioned approximately aligned with the longitudinal axis and on the second side and midway between the at least two apertures, the at least one aperture has a flow rate that is less than the equivalent flow rates of the at least two apertures, each aperture defines an axis and each axis diverges from the other axes of the plurality of apertures, the size and alignment of each aperture defines a harvest zone of that aperture and the plurality of apertures defines an array of harvest zones;
   a handle connected to the proximal end portion, the external interface adapted to provide a fluid tight coupling with an external source of reduced pressure.

2. The spinal aspiration apparatus of claim 1, wherein the first side of the distal end portion includes a plurality of apertures and at least two of the plurality of apertures are adapted to draw an approximately equivalent first flow rate and a second at least two apertures of the plurality of apertures on the first side draw a predetermined rate of flow that is not equivalent when an external source of reduced pressure is applied through the external interface.

3. The spinal aspiration apparatus of claim 2, wherein at least one aperture is defined in the second side and is adapted to draw a second flow rate when the external source of reduced pressure is applied, the second flow rate is less than the first flow rate and additional apertures are defined in the third side and the fourth side of the distal end portion.

4. The spinal aspiration apparatus of claim 1, wherein the external source of reduced pressure includes an anti-coagulant.

5. The spinal aspiration apparatus of claim 1, wherein the needle includes a valve that opens and closes the lumen.

6. The spinal aspiration apparatus of claim 1, wherein the needle includes a visible portion that provides visibility into the lumen of the needle.

7. The spinal aspiration apparatus of claim 1, wherein aspiration apparatus has a first position external to a vertebra and a second position wherein the distal end portion of the needle is adapted to be positioned at a predetermined location in a vertebral body and is adapted to be in fluid communication with the external source of reduced pressure, the plurality of diverging apertures define an array of harvest zones that differ in flow rate depending upon the location and angular direction of each aperture on the distal end portion and the predetermined location of the distal end portion in the vertebral body.

8. The spinal aspiration apparatus of claim 1, wherein the external interface defines a receptacle in the handle and a second needle recessed in the receptacle with an approximately proximally directed penetrating point, the second needle includes a port that is in fluid communication with the lumen of the needle, the receptacle and needle adapted to interface with a sealed vial that is a source of reduced pressure.

9. The spinal aspiration apparatus of claim 8, wherein the receptacle of the external interface includes a retention mechanism that is adapted to selectively retain the vial in position in the receptacle and release the vial for removal from the receptacle.

10. A method of aspirating a vertebra comprising the steps of:
   providing an aspiration apparatus that includes a needle that has a distal end portion and a proximal end portion, the distal end portion has a solid tip and a tapered shape adapted for penetrating through a pedicle pathway, the proximal end portion including an external interface, the needle defines a lumen that is in fluid communication with a plurality of diverging apertures in the distal end portion and the external interface, each aperture of the plurality of apertures has diverging directional orientations in the distal end portion relative to each of the other apertures of the plurality of apertures, at least one side of the distal end portion includes at least two apertures of the plurality of apertures, the at least two apertures include one aperture with a proximal directional orientation and one aperture with a distal directional orientation, each aperture of the plurality of apertures defines a harvest zone that diverges from the harvest zones of each of the other apertures of the plurality of apertures, the external interface adapted to provide a fluid tight coupling with an external source of reduced pressure, a handle connected to the proximal end portion;

positioning the distal end portion of the aspiration apparatus through the pedicle pathway of a vertebra and positioning the distal end portion at a predetermined location in a vertebral body; and introducing an external source of reduced pressure through the external interface, the plurality of diverging apertures in the distal end portion defining an array of diverging harvest zones and harvesting the marrow of the vertebra from the location in the vertebral body.

11. The method of aspirating a vertebra of claim 10 further comprising controlling the application of the source of reduced pressure using a valve connected to a lumen of the needle.

12. The method of aspirating a vertebra of claim 10, wherein the step of using further comprises finding the pedicle pathway.

13. The method of aspirating a vertebra of claim 10, wherein the step of introducing an external source of reduced pressure includes the plurality of diverging apertures defining an array of harvest zones that differ in flow rate depending upon their location and angular direction from the predetermined location in the vertebral body.

14. The method of aspirating a vertebra of claim 10, wherein the step of introducing further comprises the harvesting of approximately one half of the marrow of the vertebra and monitoring the quality of the harvested marrow through a portion of the needle.

15. The spinal aspiration apparatus of claim 1, wherein the needle includes a neck that has a reduced diameter, the neck separates a proximal end portion of the distal end portion and the shaft, the lumen extends through the neck to the distal end portion, the lumen in fluid communication with the plurality of apertures in the distal end portion.

16. The spinal aspiration apparatus of claim 1, wherein the plurality of apertures on the distal end portion is adapted for the harvesting of approximately one-half of the bone marrow from a vertebra from a single location in the vertebra.

17. A spinal aspiration apparatus adapted for the harvesting of bone marrow from a vertebra, the spinal aspiration apparatus comprises:

a tubular needle that includes a distal end portion and a proximal end portion that are connected by a shaft, the proximal end portion includes an external interface, the external interface adapted to provide a fluid tight coupling with an external source of reduced pressure, the needle defines a lumen that is in fluid communication with the external interface, the distal end portion, shaft and proximal end portion define a longitudinal axis, the distal end portion has a tubular wall that includes a first side, an opposed second side, a third side and a fourth side, the distal end portion has angular arcuate shape, the first side is directed radially inwardly towards the center of the arcuate shape of the distal end portion and the second side is directed radially outwardly from the center of the arcuate shape of the distal end portion, the distal end portion has a distally directed taper that terminates in a solid tip and is adapted to penetrate through a pedicle pathway to a vertebra; and a plurality of apertures defined in the distal end portion, the plurality of apertures in fluid communication with the lumen, at least two apertures of the plurality of apertures defined on one of the sides of the distal end portion, the at least two apertures have an approximately equivalent flow rate, the at least two apertures on one of the sides of the distal end portion have directional orientations that include one aperture with a proximal orientation and one aperture with a distal orientation, the at least two apertures on one of the sides of the distal end portion have directional alignments that are oblique to the longitudinal axis, the first side includes the at least two apertures with directional alignments that diverge from one another and the second side includes at least one aperture, the size of each aperture of the at least two apertures on the first side of the distal end portion is varied to define approximately equivalent flow rates, each aperture defines an axis and each axis diverges from the other axes of the plurality of apertures, the size and alignment of each aperture defines a harvest zone of that aperture and the plurality of apertures defines an array of harvest zones.

18. The spinal aspiration apparatus of claim 17, wherein the at least two apertures are positioned approximately in alignment with the longitudinal axis, the at least one aperture is positioned approximately aligned with the longitudinal axis on the second side and midway between the at least two apertures and the at least two apertures can extend at least partially onto adjoining sides of the distal end portion.

19. The spinal aspiration apparatus of claim 17, wherein the first side of the distal end portion includes a plurality of apertures and at least two of the plurality of apertures are adapted to draw an approximately equivalent first flow rate and a second at least two apertures of the plurality of apertures on the first side draw a predetermined rate of flow that is not equivalent when an external source of reduced pressure is applied through the external interface.

20. The spinal aspiration apparatus of claim 17, wherein the third side and fourth side of the distal end portion also include at least one aperture.

* * * * *